(12) United States Patent
Heuer

(10) Patent No.: US 9,464,164 B2
(45) Date of Patent: Oct. 11, 2016

(54) METHOD FOR THE PREPARATION OF POLYESTERS

(75) Inventor: Lutz Heuer, Dormagen (DE)

(73) Assignee: LANXESS Deutschland GmbH, Cologne (DE)

( * ) Notice: Subject to any disclaimer, the term of this patent is extended or adjusted under 35 U.S.C. 154(b) by 182 days.

(21) Appl. No.: 13/259,163

(22) PCT Filed: Mar. 18, 2010

(86) PCT No.: PCT/EP2010/053507
§ 371 (c)(1),
(2), (4) Date: Jan. 4, 2012

(87) PCT Pub. No.: WO2010/108840
PCT Pub. Date: Sep. 30, 2010

(65) Prior Publication Data
US 2012/0101252 A1  Apr. 26, 2012

(30) Foreign Application Priority Data

Mar. 26, 2009 (DE) .................. 10 2009 014 411

(51) Int. Cl.
| | | |
|---|---|---|
| *C08G 63/12* | (2006.01) | |
| *C08K 5/13* | (2006.01) | |
| *C08K 5/36* | (2006.01) | |
| *C08G 63/19* | (2006.01) | |
| *C08G 63/78* | (2006.01) | |
| *C08G 63/193* | (2006.01) | |
| *C08G 63/672* | (2006.01) | |
| *C08G 63/133* | (2006.01) | |
| *C08G 63/20* | (2006.01) | |
| *C08G 63/16* | (2006.01) | |
| *C07C 29/94* | (2006.01) | |
| *C07C 41/58* | (2006.01) | |
| *C08K 5/375* | (2006.01) | |

(52) U.S. Cl.
CPC .............. *C08G 63/12* (2013.01); *C07C 29/94* (2013.01); *C07C 41/58* (2013.01); *C08G 63/133* (2013.01); *C08G 63/16* (2013.01); *C08G 63/19* (2013.01); *C08G 63/193* (2013.01); *C08G 63/20* (2013.01); *C08G 63/672* (2013.01); *C08G 63/78* (2013.01); *C08K 5/13* (2013.01); *C08K 5/36* (2013.01); *C08K 5/375* (2013.01); *C07C 2101/14* (2013.01)

(58) Field of Classification Search
CPC .......... C08K 5/13; C08K 5/36; C08G 63/12; C08G 63/133; C08G 63/16; C08G 63/19; C08G 63/193; C08G 63/20; C08G 63/672; C08G 63/78
USPC .......... 252/182.24, 182.25, 182.29; 568/580, 568/701; 528/274
See application file for complete search history.

(56) References Cited

U.S. PATENT DOCUMENTS

| | | | |
|---|---|---|---|
| 4,007,230 A | 2/1977 | Hinze | |
| 4,070,304 A | 1/1978 | Hinze | |
| 4,162,363 A | 7/1979 | Stapp | |
| 5,143,943 A | 9/1992 | Suhoza et al. | |
| 5,310,782 A | 5/1994 | Takiyama et al. | |
| 5,338,478 A * | 8/1994 | Barry et al. | ............. 252/182.27 |
| 6,063,957 A * | 5/2000 | Koniger et al. | ............. 560/218 |
| 6,075,065 A | 6/2000 | Yamazaki et al. | |

(Continued)

FOREIGN PATENT DOCUMENTS

| | | |
|---|---|---|
| FR | 2246526 A1 | 5/1975 |
| GB | 2015505 A | 9/1979 |

(Continued)

OTHER PUBLICATIONS

Sax et al.; Hawley's Condensed Chemical Dictionary, Eleventh Edition; Van Nostrand Reinhold; New York; 1987; p. 934.*
International Search Report dated May 10, 2010 for WO 2010/108840 (3 pages).
Zahn et al., "Weitere Oligoester der Terephthalsaure mit Glykol", Makromol. Chem. (1959) 29(1):70-92 (English Abstract Only).
BASF Intermediates, "PolyTHF: Supporting Your Growth", BASF Corporation, 2015, available at http://www.basf.de/intermediates.

(Continued)

*Primary Examiner* — Rabon Sergent

(57) ABSTRACT

Disclosed is a method for preparing polyesters, comprising reacting polyols with carboxylic acids and, optionally, a catalyst, wherein the polyols bear at least two hydroxyl groups, wherein, at least one of said hydroxyl group is bound to an aliphatic carbon atom and wherein the polyols comprise one or more compounds of the formula (I) or (II),

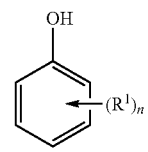
(I)

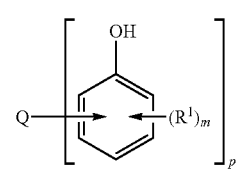

(II)

where
n is 1, 2, 3 or 4,
m is 1, 2 or 3,
p is 2,
Q is sulphur or $C_1$-$C_4$-alkylene, and
the radicals $R^1$ are each, independently of any other radicals $R^1$ present, $C_1$-$C_8$-alkyl or $C_1$-$C_8$-alkoxy,
where at least one ortho position of the two phenyl rings in the formula (II) or the phenyl ring in the formula (I) must be substituted by a secondary or tertiary radical.

5 Claims, No Drawings

(56) References Cited

U.S. PATENT DOCUMENTS

| | | |
|---|---|---|
| 7,579,393 B2 | 8/2009 | Malz et al. |
| 2009/0182113 A1 | 7/2009 | Rodewald et al. |
| 2010/0204370 A1 | 8/2010 | Maeder |

FOREIGN PATENT DOCUMENTS

| | | |
|---|---|---|
| JP | 53108909 | 9/1978 |
| JP | 6128364 A | 5/1994 |
| WO | 9965850 A1 | 12/1999 |

* cited by examiner

METHOD FOR THE PREPARATION OF POLYESTERS

The invention relates to a method of stabilizing polyols and also mixtures containing polyols and stabilizers.

Polyols, in particular aliphatic dihydroxy, trihydroxy or tetrahydroxy compounds, have great importance in industry because of their many possible uses. They are oxidation-resistant under normal conditions and are therefore typically stored under air.

If such polyalcohols are then used for subsequent reactions in which acidic conditions are created, e.g. with the objective of ester formation, discolouration which makes the downstream product unusable or unsalable frequently occurs despite the typically high purity of the polyol used.

There is therefore a need for a method which reduces such undesirable discolouration.

We have now found a method of stabilizing polyols, which is characterized in that one or more compounds of the formula (I) or (II),

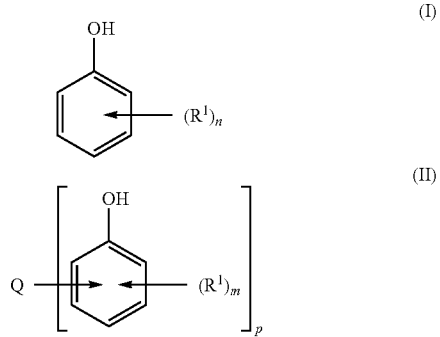

where
n is 1, 2, 3 or 4, preferably 2 or 3,
m is 1, 2 or 3, preferably 1 or 2,
p is 2,
Q is sulphur or $C_1$-$C_4$-alkylene, preferably $C_1$-$C_4$-alkylene, and
the radicals $R^1$ are each, independently of any other radicals $R^1$ present, $C_1$-$C_8$-alkyl or $C_1$-$C_8$-alkoxy,
where at least one ortho position of the two phenyl rings in the formula (II) or the phenyl ring in the formula (I) must be substituted by a secondary or tertiary radical,
are added to the polyols.

Alkyl or alkylene or alkoxy is in each case independently a straight-chain, branched or unbranched, optionally cyclic, alkyl or alkylene or alkoxy radical.

$C_1$-$C_8$-Alkyl is, for example, methyl, ethyl, n-propyl, isopropyl, n-butyl, sec-butyl and tert-butyl, n-pentyl, 1-methylbutyl, 2-methylbutyl, 3-methylbutyl, neopentyl, 1-ethylpropyl, cyclohexyl or 2-methylcyclohexyl, preferably methyl, tert-butyl or cyclohexyl.

$C_1$-$C_8$-Alkoxy is, for example, methoxy, ethoxy, n-propoxy, isopropoxy, n-butoxy, sec-butoxy and tert-butoxy, neopentoxy, cyclohexoxy, cyclopentoxy and n-hexoxy.

$C_1$-$C_4$-Alkylene is, for example, methylene, ethanediyl, 1,2-propanediyl, 1,3-propanediyl, 1,4-butanediyl, 2,3-butanediyl or 1,3-butanediyl, preferably methylene.

Preferred compounds of the formula (I) are: 2,6-bis[tert-butyl]-4-methylphenol] (BHT), 2,4,6-tri-t-butylphenol; 2- and 3-tert-butylhydroxyanisole and mixtures thereof (BHA).

Preferred compounds of the formula (II) are:
2,2'-methylenebis[4-methyl-6-(α-methylcyclohexyl)phenol], 2,2'-methylenebis [4-methyl-6-cyclohexyl)phenol] (ZKF), 2,2'-methylenebis(4-methyl-6-tert-butylphenol), 2,2'-methylenebis[6-tert-butyl-4-ethylphenol], 2,2'-methylenebis[6-tert-butyl-4-methylphenol] (BKF), 4,4'-methylenebis[2,6-di-tert-butylphenol], 4,4'-methylenebis[6-tert-butyl-2-methylphenol], with special preference being given to 2,2'-methylenebis[4-methyl-6-cyclohexyl)phenol] and 2,2'-methylenebis[6-tert-butyl-4-methylphenol].

The abovementioned compounds of the formulae (I) and (II) can be used individually or as mixtures.

For the purposes of the present invention, polyols are compounds which bear at least two, preferably two, three or four, hydroxy groups of which at least one, preferably all, is/are bound to an aliphatic carbon atom.

Preferred polyols are aliphatic polyols such as 1,4-butanediol, 1,5-pentanediol, 1,6-hexanediol, octane-1,8-diol, decane-1,10-diol, trimethylolpropane, ditrimethylolpropane, pentaerythritol, neopentyl glycol, ethylene glycol, diethylene glycol, triethylene glycol, tetraethylene glycol, polyethylene glycol, 1,3-butylene glycol and 1,4-cyclohexanediol or mixtures thereof.

Particularly preferred polyols are 1,6-hexanediol, octane-1,8-diol, decane-1,10-diol, trimethylolpropane, ditrimethylolpropane, pentaerythritol, 1,4-cyclohexanediol or mixtures thereof.

Very particularly preferred polyols are hexane-1,6-diol and trimethylolpropane.

The total amount of compounds of the formulae (I) and (II) added is, for example, from 0.0001 to 60% by weight, preferably from 0.0001 to 2.0% by weight, particularly preferably from 0.001 to 1.0% by weight, very particularly preferably from 0.001 to 0.1% by weight and even more preferably from 0.002 to 0.8% by weight.

The invention also encompasses mixtures containing polyols and at least one compound of the formula (I) or (II).

Preference is given to mixtures containing polyols and at least one compound of the formula (I) or (II) in which the proportion by weight of the polyols is at least 40%, preferably at least 90%, particularly preferably at least 95% and very particularly preferably at least 98%, and the total content of compounds of the formulae (I) and (II) in the mixture is from 0.0001 to 60% by weight, preferably from 0.0001 to 2.0% by weight, particularly preferably from 0.001 to 1.0% by weight, very particularly preferably from 0.001 to 0.1% by weight and even more preferably from 0.002 to 0.8% by weight.

Mixtures having a high content of compound of the formula (I) or (II) can also be used as masterbatch in order to achieve the final concentrations mentioned above in preferred ranges more easily, and these are likewise preferred as raw material for the ready-to-use mixtures.

The mixtures of the invention can be solid or liquid.

The mixtures of the invention preferably contain 2% by weight or less, preferably 1% by weight or less, of materials which are not polyols or compounds of the formula (I) or (II).

Among the abovementioned mixtures, particular preference is given to those in which the polyols are selected from the group consisting of: preferred polyols are 1,6-hexanediol, 1,4-butanediol, pentaerythritol, neopentyl glycol, trimethylolpropane, pentaerythritol, polyethylene glycol, 1,3-butylene glycol.

The polyols which have been stabilized in this way or the mixtures of the invention are particularly suitable in a process for preparing polyesters, preferably a process carried out under acidic conditions, where the term "acidic"

refers to a pH which, based on an aqueous comparative scale under standard conditions, is less than 7.0. The abovementioned preferred ranges for the contents of polyols and compounds of the formulae (I) and (II) apply in the same way.

Such processes for preparing polyesters are adequately known to those skilled in the art and comprise, for example, the preparation of polyesters by reaction of polyols with polycarboxylic acids with elimination of water, optionally in the presence of catalysts. The reaction temperatures here can be, for example, from 20° to 240° C., preferably from 40 to 190° C.

The compounds of the formulae (I) and (II) which are added surprisingly have no adverse effect on the esterification process but largely avoid undesirable discolouration even at high process temperatures. According to the invention, it is normally possible to limit the discolouration to a colour number of less 100 APHA, preferably to 60 or less.

The invention is illustrated by the Examples without being restricted thereto.

EXPERIMENTS 100 g in each case of the mixture of 1,6-hexanediol and stabilizer to be examined were placed in a 1 l four-neck flask and heated by means of a heating mantle at 130° C. for 4 hours while stirring. 100 g of adipic acid was subsequently introduced into the resulting melt while continually passing nitrogen over the melt, resulting in the melt cooling to about 80-90° C. The mixture was subsequently heated to 175° C. over a period of 5 minutes and allowed to react at this temperature for 10 minutes. The water vapour formed in the esterification was discharged. After the end of the reaction time, the colour number of the melt was determined at 130° C. in an 11 mm round cuvette. Calibration was in each case carried out against water (APHA colour number=0), in each case immediately before the measurement.

The experimental results are summarized in the following table:

| Example | Amount | Stabilizer | APHA colour number |
|---|---|---|---|
| 1 | 0 | none | 700 |
| 2** | 0.05% | Cyclohexen-3-ylidenemethyl benzyl ether | 500 |
| 3** | 0.05% | Pentaerythritol bis [cyclohexen-3-yl-1-formyl]acetal | 100 |
| 4 | 1% | 2,6-Bis[tert-butyl]-4-methylphenol] | 15 |
| 5* | 0.1% | 2,6-Bis[tert-butyl]-4-methylphenol] | 18 |
| 6 | 0.05% | 2,6-Bis[tert-butyl]-4-methylphenol] | 9 |
| 7 | 0.025% | 2,6-Bis[tert-butyl]-4-methylphenol] | 23 |
| 8 | 0.01% | 2,6-Bis[tert-butyl]-4-methylphenol] | 56 |
| 9 | 0.025% | 2,2'-Methylenebis[6-tert-butyl-4-methylphenol] | 50 |
| 10 | 0.025% | 2,2'-Methylenebis[4-methyl-6-cyclohexylphenol] | 60 |
| 11** | 0.025% | Mixture of alkylated styrylphenols | 500 |
| 12** | 0.025% | Mixture of styrylphenols | 700 |
| 13 | 0.025% | Mixture of 2- and 3-tert-butylhydroxyanisole | 60 |

*use of caproic acid instead of adipic acid
**examples for comparison

Antioxidants used for examples which are not according to the invention:

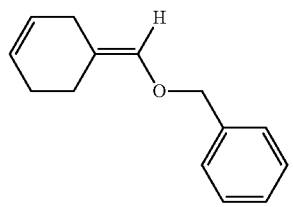

Cyclohexen-3-ylidenemethyl benzyl ether

Pentaerythritol bis[cyclohexen-3-yl-1-formyl]acetal

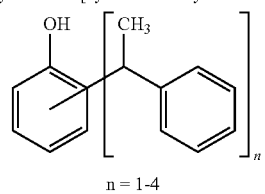

n = 1-4
Mixture of styrylphenols

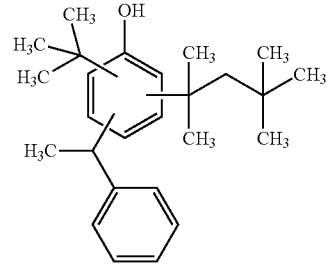

Mixture of alkylated styrylphenols

What is claimed is:

1. A method for preparing polyester from stabilized polyols and polycarboxylic acid, the method comprising:
stabilizing one or more polyols selected from a group consisting of 1,4-butanediol, 1,5-pentanediol, 1,6-hexanediol, octane-1,8-diol, decane-1,10-diol, trimethylolpropane, ditrimethyiolpropane, pentaerythritol, neopentyl glycol, ethylene glycol, diethylene triethylene glycol, tetraethylene glycol, 1,3-butylene glycol and 1,4-cyclohexanediol or mixtures thereof, by contacting the polyols with one or more compounds of the formula (I) or (II) to produce a first mixture containing stabilized polyols,

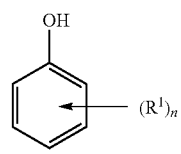

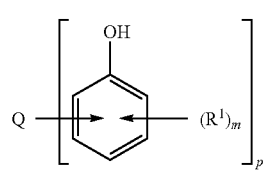

where:
n is 1, 2, 3 or 4,
m is 1, 2 or 3,
p is 2,
Q is sulphur or methylene, and
the radicals $R^1$ are each, independently of any other radicals $R^1$ present, $C_1$-$C_8$-alkyl or $C_1$-$C_8$-alkoxy,
where at least one ortho position of the two phenyl rings in the formula (II) or the phenyl ring in the formula (I) must be substituted by a secondary or tertiary radical; and
subsequent to producing the first mixture of stabilized polyols, contacting one or more polycarboxylic adds with the first mixture of stabilized polyols to form a second mixture and produce polyesters from the stabilized polyols and the polycarboxylic acid.

2. Method according to claim 1, wherein the one or more compounds of formula (I) or (II) comprise 2,6-bis[tert-butyl]-4-methylphenol] (BHT), 2,4,6-tri-t-butylphenol, 2- and 3-tert-butylhydroxyanisole and mixtures thereof (BHA), 2,2'-methylenebis[4-metnyl-6-(α-methylcyclohexyl)phenol], 2,2'-methylenebis[4-methyl -6-cyclohexyl)phenol] (ZKF), 2,2'-methylenebis(4-methyl-6-tert-butylphenol), 2,2'-methylenebis[6-tert-butyl-4-ethylphenel], 2,2'-methylenebis[6-tert-butyl-4-methyl -phenol] (BKF), 4,4'-methylenebis[2,6-di-tert-butylphenol], 4,4'-methylenebis[6-tert-butyl -2-methylphenol] or mixtures thereof.

3. The method according to claim 1, wherein the polycarboxylic acid is adipic acid.

4. The method of claim 1, wherein, based on the weight of the first mixture, the first mixture comprises:
at least 40 wt % of the one or more polyols: and
0.001 to 60 wt % of the one or more compounds of formula (I) or formula (II).

5. A method for preparing polyester from polycarboxylic acid and stabilized polyols, the method comprising:
contacting one or more aliphatic polyols with one or more compounds of the formula (I) or (II)

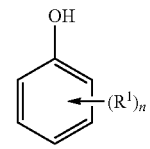
(I)

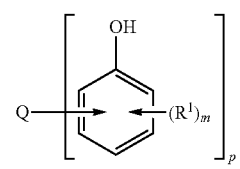
(II)

where:
n is 1, 2, 3 or 4,
m is 1, 2 or 3,
p is 2,
Q is sulphur or $C_1$-$C_4$alkylene,
the radicals $R^1$ are each, independently of any other radicals $R^1$ present, $C_1$-$C_8$-alkyl or $C_1$-$C_8$-alkoxy, and
where at least one ortho position of the two phenyl rings in the formula (II) or the phenyl ring in the formula (I) must be substituted by a secondary or tertiary radical,
to stabilise the one or more polyols and produce stabilized polyols;
contacting arm or more poiycarboxylic acids and the stabilized polyols produce a reaction mixture, and esterifying the polycarboxylic acids and stabilized polyols to produce polyesters.

* * * * *